(12) United States Patent
Harmer et al.

(10) Patent No.: US 6,281,400 B1
(45) Date of Patent: Aug. 28, 2001

(54) PROCESS FOR PREPARATION OF A CATALYTIC MICROCOMPOSITE FROM A SILICATE AND A HIGHLY FLUORINATED ION EXCHANGE RESIN

(75) Inventors: Mark Andrew Harmer, Kennett Square, PA (US); Qun Sun, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/462,970

(22) PCT Filed: Jul. 29, 1998

(86) PCT No.: PCT/US98/15760

§ 371 Date: Jan. 14, 2000

§ 102(e) Date: Jan. 14, 2000

(87) PCT Pub. No.: WO99/06145

PCT Pub. Date: Feb. 11, 1999

Related U.S. Application Data (60) Provisional application No. 60/054,102, filed on Jul. 29, 1997.

(51) Int. Cl.[7] .............................. C07C 5/23; C07C 45/53; C07C 49/786; B01J 31/10
(52) U.S. Cl. .................. 585/457; 585/458; 585/462; 585/668; 585/669; 568/322; 568/323; 568/485; 568/768; 568/798; 502/159; 502/402; 521/28
(58) Field of Search ................................. 502/159, 402; 521/25, 28; 585/664, 666, 669, 670, 457, 458, 668, 462; 568/798, 485, 741, 768

(56) References Cited

U.S. PATENT DOCUMENTS

| 4,038,213 | 7/1977 | McClure et al. ...................... 252/430 |
| 4,870,217 | 9/1989 | Knifton ................................. 568/798 |
| 4,876,397 | 10/1989 | Knifton et al. ....................... 568/798 |
| 4,898,995 | 2/1990 | Knifton et al. ....................... 568/798 |
| 5,094,995 | * 3/1992 | Butt et al. ............................. 502/402 |
| 5,824,622 | * 10/1998 | Harmer et al. ....................... 502/407 |
| 5,916,837 | * 6/1999 | Harmer et al. ....................... 502/170 |
| 5,932,511 | * 8/1999 | Harmer et al. ....................... 502/159 |
| 5,948,946 | * 9/1999 | Harmer et al. ....................... 585/669 |
| 5,958,822 | * 9/1999 | Beckerbauer et al. ............... 502/168 |
| 6,034,290 | * 3/2000 | Harmer et al. ....................... 570/236 |
| 6,107,233 | * 8/2000 | Harmer et al. ....................... 502/159 |

FOREIGN PATENT DOCUMENTS

| WO 91/01805 | 2/1991 | (WO) | .............................. B01J/31/10 |
| WO 95/19222 | 7/1995 | (WO) | .............................. B01J/31/10 |
| WO 96/19228 | 6/1996 | (WO) | .............................. A61K/31/60 |
| WO 97/35662 | 10/1997 | (WO) | .............................. B01J/31/10 |

* cited by examiner

Primary Examiner—Bekir L. Yildirim (57) ABSTRACT

The present invention relates to a process for preparing a microcomposite comprising a highly fluorinated ion-exchange polymer containing pendant sulfonate functional groups, said polymer existing as aggregated particles entrapped within and dispersed throughout a network of silica. Due to their high surface area and acid functionality, these microcomposites possess wide utility as improved solid acid catalysts, particularly in the substitution of aromatic compounds, in the decomposition of hydroperoxides, and in the isomerization of olefins.

10 Claims, 3 Drawing Sheets

PROCESS FOR PREPARATION OF A CATALYTIC MICROCOMPOSITE FROM A SILICATE AND A HIGHLY FLUORINATED ION EXCHANGE RESIN

CROSS-REFERENCE TO RELATED APPLICATIONS

This application was filed under 35 U.S.C. 371 from International Application No. PCT/US98/15760 filed Jul. 29, 1998, which claims priority benefit from application Ser. No. 60/054,102, filed Jul. 29, 1997.

BACKGROUND OF THE INVENTION

The present invention relates to a process for preparing a microcomposite comprising a highly fluorinated ion-exchange polymer containing pendant sulfonate functional groups, said polymer existing as aggregated particles entrapped within and dispersed throughout a silica network. Due to their high surface area and acid functionality, these microcomposites possess utility as improved solid acid catalysts.

A microcomposite comprising perfluorinated ion-exchange polymers (PFIEP) containing pendant sulfonic acid groups and/or pendant carboxylic acid groups entrapped within and highly dispersed throughout a metal oxide network and its preparation are disclosed in WO95/19222. The microcomposites described therein are prepared using PFIEP in water and alcohol.

Alkylation of aromatics is practiced in many segments of the chemical industry. Around 2.5 MM tons of linear alkylbenzene is produced each year which is used for making detergents. The reaction is usually catalyzed by liquid HF and $H_2SO_4$. In addition, approximately 2 MM tons of phenol and 100 MMlb of hydroquinone are produced by the $H_2SO_4$ catalyzed decomposition of the corresponding hydroperoxides. The acid reaction medium is highly corrosive and the decomposition processes can become violent and produce by-product black tars. Further, the Friedel-Crafts acylations of aromatics are currently often catalyzed by Lewis acid, such as $AlCl_3$, $ZnCl_2$ and $BF_3$, which generates high volume waste streams. It is desirable to find a clean and effective solid acid catalyst for these and other processes.

It is an object of the present invention to provide a microcomposite that possesses high catalytic activity for a variety of applications.

SUMMARY OF THE INVENTION

The present invention provides a process for the preparation of a porous microcomposite which comprises a highly fluorinated ion-exchange polymer containing pendant sulfonate functional groups, said polymer existing as aggregated particles entrapped within and dispersed throughout a network of silica, wherein the weight percentage of the highly fluorinated ion-exchange polymer in the microcomposite is from about 0.1 to about 90 percent, and a first set of pores have an average pore diameter ranging from about 0.5 nm to about 75 nm, said process comprising the steps of:

(a) preparing a liquid composition consisting essentially of water and a highly fluorinated ion-exchange polymer containing pendant sulfonate functional groups;

(b) contacting said liquid composition with a solution consisting essentially of water and a silicate selected from the group consisting of: sodium silicate, ammonium silicate, potassium silicate, and any combinations thereof;

(c) allowing the silicate to form a network of silica; and (d) recovering the porous microcomposite.

In a separate embodiment, the microcomposite can simultaneously contain a second set of larger pores ranging from about 75 nm to about 1000 nm, wherein these larger pores are formed by introducing acid-extractable filler particles during the formation process.

The present invention also provides a porous microcomposite prepared by the above process.

The present invention further provides an improved process for the following reactions wherein the improvement comprises using a catalytic amount of a microcomposite prepared by the above process: olefin isomerization; decomposition of cumene hydroperoxide; and aromatic substitution, such as aromatic alkylation, and Friedel-Crafts acylation.

DETAILED DESCRIPTION

This invention is directed to a process for preparing a porous microcomposite having a diameter of about 0.1 to about 1.0 mm, a specific surface area of about 10 to about 800 $m^2/g$, and a specific pore volume of about 0.2 to about 3.0 cc/g. The microcomposite comprises a highly fluorinated ion-exchange polymer containing pendant sulfonate functional groups, said polymer existing as aggregated particles entrapped within and dispersed throughout a network of silica, wherein the weight percentage of the highly fluorinated ion-exchange polymer in the microcomposite is from about 0.1 to about 90 percent. The process comprises the steps of: (a) preparing a liquid composition consisting essentially of water and a highly fluorinated ion-exchange polymer containing pendant sulfonate functional groups; (b) contacting said liquid composition with a solution consisting essentially of water and a silicate selected form the group consisting of: sodium silicate, ammonium silicate, potassium silicate, and any combination thereof; (c) allowing the silicate to form a network of silica; and (d) recovering the porous microcomposite.

It has been found that by using a highly fluorinated ion-exchange resin in water only and a silicate as a silica network precursor, the product microcomposite can show higher activity (by a factor of at least 10 for certain applications) than a similar microcomposite made previously using PFIEP resin in a water/alcohol solution and various silica sources.

In step (a) of the process of the present invention, a liquid composition is prepared consisting essentially of water and a highly fluorinated ion-exchange polymer containing pendant sulfonate functional groups. The liquid composition can be prepared by taking a commercial highly fluorinated ion exchange polymer solution, or a solution of such polymer that is prepared via techniques known in the art, and removing the alcohol or other organic solvents via conventional techniques known to those of ordinary skill in the art, such as distillation. The polymer solution can also be prepared from polymer resin in water only as described in more detail below.

Polymers for use in accordance with the present invention are highly fluorinated ion-exchange polymers having sulfonate functional groups. "Highly fluorinated" means that at least 90% of the total number of halogen and hydrogen atoms in the polymer are fluorine atoms. Most preferably the polymer is perfluorinated. The term "sulfonate functional groups" is intended to refer to either to sulfonic acid groups or salts of sulfonic acid groups, preferably alkali metal or ammonium salts. Most preferably, the functional groups are represented by the formula —$SO_3X$ wherein X is H, Li, Na, K or $N(R^1)(R^2)(R^3)(R^4)$ and $R^1$, $R^2$, $R^3$, and $R^4$ are the same or different and are H, $CH_3$ or $C_2H_5$. For applications where the polymer is to be used for proton exchange, the sulfonic acid form of the polymer is preferred, i.e., where X is H in the formula above.

Preferably, the polymer comprises a polymer backbone with recurring side chains attached to the backbone with the side chains carrying the sulfonate functional groups. Possible polymers include homopolymers or copolymers of two or more monomers. Copolymers are typically formed from one monomer which is a nonfunctional monomer and which provides carbon atoms for the polymer backbone. A second monomer provides both carbon atoms for the polymer backbone and also contributes the side chain carrying the cation exchange group or its precursor, e.g. a sulfonyl fluoride group (—$SO_2F$), which can be subsequently hydrolyzed to a sulfonate functional group. For example, copolymers of a first fluorinated vinyl monomer together with a second fluorinated vinyl monomer having a sulfonyl fluoride group (—$SO_2F$) can be used. Possible first monomers include tetrafuoroethylene (TFE), hexafluoropropylene, vinyl fluoride, vinylidine fluoride, trifluoroethylene, chlorotrifluoroethylene, perfluoro (alkyl vinyl ether), and mixtures thereof Possible second monomers include a variety of fluorinated vinyl ethers with sulfonate functional groups or precursor groups which can provide the desired side chain in the polymer. The first monomer may also have a side chain in the polymer. The first monomer may also have a side chain which does not interfere with the ion exchange function of the sulfonate functional group. Additional monomers can also be incorporated into these polymers if desired.

A class of preferred polymers for use in the present invention include a highly fluorinated, most preferably perfluorinated, carbon backbone and a side chain which is represented by the formula —(O—$CF_2CFR_f)_a$—O—$CF_2CFR'_fSO_3X$, wherein $R_f$ and $R'_f$ are independently selected from F, Cl or a perfluorinated alkyl group having 1 to 10 carbon atoms, a=1, 2 or 3, and X is H, Li, Na, K or $N(R^1)(R^2)(R^3)(R^4)$ and $R^1$, $R^2$, $R^3$, and $R^4$ are the same or different and are H, $CH_3$ or $C_2H_5$. The preferred polymers include, for example, polymers disclosed in U.S. Pat. No. 3,282,975 and in U.S. Pat. Nos. 3,358,545 and 4,940,525. One preferred polymer comprises a perfluorocarbon backbone and a side chain which is represented by the formula —O—$CF_2CF(CF_3)$—O—$CF_2CF_2SO_3X$, wherein X is as defined above. Polymers of this type are disclosed in U.S. Pat. No. 3,282,875 and can be made by copolymerization of tetrafluoroethylene (TFE) and the perfluorinated vinyl ether $CF_2$=CF—O—$CF_2CF(CF_3)$—O—$CF_2CF_2SO_2F$, perfluoro (3,6-dioxa-4-methyl-7-octenesulfonyl fluoride) (followed by conversion to sulfonate groups by hydrolysis of the sulfonyl fluoride groups and ion exchanging if needed to convert to the desired form). One preferred polymer of the type disclosed in U.S. Pat. Nos. 4,358,545 and 4,940,525 has the side chain —O—$CF_2CF_2SO_3X$, wherein X is as defined above. This polymer can be made by copolymerization of TFE and the perfluorinated vinyl ether $CF_2$=CF=O—$CF_2CF_2SO_2F$, perfluoro(3-oxa-4-pentenesulfonyl fluoride) followed by hydrolysis and ion exchange if needed.

The polymers have an equivalent weight of less than about 2000. For the purposes of this application, equivalent weight is defined to be the weight of the polymer in sulfonic acid form required to neutralize one equivalent of NaOH. Within the range of less than about 2000, the equivalent weight of the cation exchange polymer will vary with the molecular weight of the monomer or monomers used but can be varied as desired for the particular application. With most polymers, the equivalent weight is preferably about 500 to about 2000. In the case where the polymer comprises a perfluorocarbon backbone and the side chain is the salt of —O—$CF_2CF(CF_3)$—O—$CF_2CF_2SO_3X$, the equivalent weight preferably is at least about 750, most preferably about 750 to about 1500. The equivalent weight of the polymers having the side chain —O—$CF_2CF_2SO_3X$ is often lower in many applications because of the lower molecular weight of the monomer unit containing the sulfonate functional group. Preferably, the equivalent weight is at least about 650, most preferably about 650 to about 1400.

The highly fluorinated ion exchange polymer containing pendant sulfonate functional groups used in the present invention are well known compounds. See, for example, Waller et al., Chemtech, July 1987, pp. 438–441, and references therein, and U.S. Pat. No. 5,094,995, incorporated herein by reference. Polymers discussed by J. D. Weaver et al., in Catalysis Today, 14 (1992) 195–210, are also useful in the present invention. Other perfluorinated polymer sulfonic acid catalysts are described in Synthesis, G. I. Olah, P. S. Iyer, G. K. Surya Prakash, 513–531 (1986). Perfluorinated polymers used in membranes, such as NAFION®, are commercially available from E. I. du Pont de Nemours and Company, and polymers, or derivatives of polymers, are disclosed in U.S. Pat. Nos. 3,282,875; 4,329, 435; 4,330,654; 4,358,545; 4,417,969; 4,610,762; 4,433, 082; and 5,094,995.

There are also several additional classes of polymer catalysts associated with metal cation ion-exchange polymers and useful in preparing the microcomposite of the present invention. These comprise 1) a partially cation-exchanged polymer, 2) a completely cation-exchanged polymer, and 3) a cation-exchanged polymer where the metal cation is coordinated to another ligand (see U.S. Pat. No. 4,414,409, and Waller, F. J. in Polymeric Reagents and Catalysts; Ford, W. T., Ed.; ACS Symposium Series 308; American Chemical Society; Washington, DC, 1986, Chapter 3).

The highly fluorinated ion-exchange polymers are used within the context of the present invention in a liquid composition form (also called a solution) which can be prepared using the process in U.S. Pat. No. 4,433,082 or Martin et al., Anal. Chem., Vol. 54, pp 1639–141(1982) incorporated by reference herein and then modified as needed to remove a portion of the water, alcohols or any volatile organic by-products by distillation or other methods known in the art to give a liquid composition consisting essentially of the water and the polymer. Formation of the liquid composition of polymer can be made at a temperature ranging from about 0° C. to about 100° C. with atmospheric pressure for those liquid composition originating with an alcohol/water PFIEP solution.

Commercially available liquid compositions of perfluorinated ion-exchange polymer can be used in the preparation of the water/polymer liquid composition used in the process of the present invention (e.g., a 5 wt % solution of a perfluorinated ion-exchange powder in a mixture of lower aliphatic alcohols and water, Cat. No. 27,470-4, Aldrich Chemical Company, Inc., 940 West Saint Paul Avenue, Milwaukee, Wis. 53233). These commercial compositions can then be modified to remove excess water, any alcohol, or other organic co-solvents to provide the liquid composition used in the process of the present invention which consists essentially of polymer and water.

The liquid composition of polymer can also be prepared from an aqueous liquid composition comprising particles of highly fluorinated ion-exchange polymer having sulfonate functional groups and having an equivalent weight of less than about 2000. The process includes contacting in a pressurized vessel the polymer with an aqueous liquid dispersion medium at a temperature of about 150° C. to about 300° C. The dispersion medium for use in the process is substantially free of water-miscible alcohols. The process also includes agitating the contents of the vessel sufficiently to subject the contents of the vessel to a shear of at least about 150 sec$^{-1}$, cooling the contents of the vessel to a temperature of less than about 100° C., and recovering an aqueous liquid composition comprising particles of the highly fluorinated ion-exchange polymers.

In step (b) of the present process, the liquid composition is contacted with a solution of silicate. The solution of silicate consists essentially of water and a silicate selected from the group consisting of: sodium silicate, ammonium silicate, potassium silicate, and any combination thereof.

The amount of water used in the combined silicate solution and polymer liquid composition of the present process is at least sufficient for the complete hydrolysis and condensation of any silicate that is not already hydrolyzed and/or condensed. Preferably, an excess amount of water is used as compared with the stoichiometrically required amount. The amount of water required for hydrolysis depends on the rate of hydrolysis of silicate. Generally, hydrolysis takes place more rapidly with increasing amounts of water. Hydrolysis can begin upon contact of the silicate with the water.

In step (c) of the present process, the silicate is allowed to form a network of silica. Network formation is accomplished via gelation of the silicate which may in some instances self-initiate due to the presence of the water. In other instances, network formation is allowed by initiating gelation, which can be achieved in a number of ways. Initiation of gelation and the rate of gelation are dependent on a number of factors, such as the amount of water present, pH and the nature of any acid or base catalyst used, temperature, pressure, and concentration of the silicate. The time required for the network formation can thus vary widely depending on these factors from practically instantaneous to several days.

As discussed above, a larger amount of water can increase the rate of hydrolysis and thus the eventual rate of gelation. A higher concentration of the silicate can result in a faster rate of gelation.

A catalyst can be used facilitate the network formation of the silicate via gelation by increasing or decreasing the rate of gelation once the silicate is in the presence of the liquid composition. Gelation can be carried out over a wide range of acidity and basicity. Network formation can be formed by acid catalyzed gelation (see Sol-Gel Science, Brinker, C. J. and Scherer, G. W., Academic Press, 1990). Although gels can be formed using acid only, the rate of gelation is usually slower when acids are used. Representative examples of suitable catalysts are HCl, $H_3PO_4$, $CH_3COOH$, $NH_3$, $NH_4OH$, NaOH, KOH, LiOH, organic amines, such as pyridine, and $NR^5_3$, wherein $R^5$ represents an alkyl group which contains 1 to 6 carbon atoms. The pH adjustment using either acid or base can be achieved in a number of ways and is also dependent on the concentration of acid or base employed. In order to allow network formation to occur, the acid or base can be added to either the silicate solution, to the liquid composition of PFIEP, or to the combined solutions. Agitation, such as by stirring or ultrasonication, may be used, if necessary, to effect good contact of the catalyst with the other ingredients present.

Gelation can be carried out at virtually any temperature at which the combined liquid composition and solution is initially in liquid form, preferably 0–100° C. The reaction is typically carried out at room temperature. Raising the temperature can increase the rate of gelation.

Gelling may be initiated at atmospheric pressure or at an excess pressure which corresponds to the sum of the partial pressures of the components of the reaction mixture at the particular temperature being applied. The use of atmospheric pressure is preferred.

After formation, the microcomposite may optionally be allowed to stand for a period of time. This is referred to as aging. Aging of the wet microcomposite for a few hours to about two days at about room temperature to about 200° C., preferably about 75° C., can lead to an increase in pore size and pore volume. This effect is characteristic of silica type gels, where the aging effect gives rise to an increasingly crosslinked network which upon drying is more resistant to shrinkage and thus a higher pore size and higher pore volume results (see, for example, the text Sol-Gel Science, Brinker, C. J. and Scherer, G. W., Academic Press, 1990, pp. 518–523).

In step (d), the solid, porous microcomposite formed is recovered after a sufficient reaction time, at a temperature ranging from room temperature to about 250° C. A sufficient reaction time is the time needed for the microcomposite to harden sufficiently to maintain its shape when recovered. Recovery of the microcomposite can be accomplished by decanting, filtering or centrifuging.

After recovery and optional aging, the microcomposites can be optionally dried at a temperature ranging from room temperature to about 250° C., optionally under a protective gas or under vacuum, for a time sufficient to further harden and stabilize the microcomposites. Drying can take place from about 1 hour to about one week.

Preferably, following removal of the water, the present process further comprises reacidification, washing, filtering or a combination thereof, of the microcomposite. Reacidification, washing, filtering or a combination thereof, may be repeated a number of times. Reacidification of the microcomposite converts, for example, the sodium salt of the perfluorosulfonic acid into the acidic, active form. Suitable acids used for reacidification comprise HCl, $H_2SO_4$ and nitric acid. Washing can be done with deionized water, and the filtering removes excess acid. Reacidification, washing, filtering, or a combination thereof can take place at a temperature ranging from room temperature to about 100° C. at atmospheric pressure, and for a time ranging from about one hour to about 24 hours.

In an alternative embodiment, macroporosity (pore sizes about 75 to about 1000 mn) is introduced into the microcomposite, resulting in a microcomposite having both increased surface area from the micropores and mesopores (0.5–75 nm) and enhanced accessibility resulting from the macropores (75–1000 nm). This macroporosity can be achieved by adding approximately 1 to 80 wt % (based upon gel weight) of acid-extractable filler particles such as calcium carbonate, to the sol-gel process prior to the gelation step. Thus, the present process further comprises at step (a) or (b) adding acid extractable filler particles in an amount from about 1 to 80 weight percent based on the ultimate gel weight. Then after step (d), the following steps are performed: (e) acidifying the product of step (d) by the addition of acid; and (f) removing the excess acid from the microcomposite. This will then yield a microcomposite further containing a second set of pores in the range of about 75 nm to about 1000 nm.

"Acid extractable filler particles" which are used in the process of the invention to introduce macropores of about 75 to about 1000 nm into the microcomposite include particles which are insoluble in the preparative gel-forming solvent, but are acid soluble and extractable from the formed microcomposite. Such filler particles include, for example, alkali metal carbonates or alkaline earth carbonates, such as calcium carbonate, sodium carbonate and potassium carbonate.

The present invention also provide a porous microcomposite produced by the above process. The porous nature of the microcomposite can be readily demonstrated, for example, by solvent absorption. The microcomposite can be observed to emit bubbles when placed in solvent which bubbles are evolved due to the displacement of the air from within the porous network. The size of the pores in the microcomposite is about 0.5 nm to about 75 mn. Preferably, the pore size is about 0.5 to about 50 nm, most preferably about 0.5 to about 30 nm.

A number of reaction variables, for example pH, temperature, aging, method of drying and drying time, have been found to affect the pore size and pore size distribution of the microcomposite. Both higher pH and longer aging of the microcomposite (before solvent removal) lead to larger final pore size in dried microcomposites.

It is believed that the porous microcomposites of the present invention comprise a network of silica within which aggregates of polymer particles are entrapped and dispersed throughout. By "aggregated particles" is meant a collection of polymer particles. By "dispersed throughout" is meant that the aggregated polymer particles are found within the silica network matrix itself and that these aggregates can be found throughout the entire network (as opposed to supported catalysts wherein the polymer catalyst exists essentially as a coating on the surface of the support, or on the surface and possibly inside the pores of the support). By "entrapped within" is meant that the polymer particles cannot be extracted from the microcomposite to any significant degree by alcohol solutions or the normal processing conditions in which the microcomposite will be used.

Figure 1:
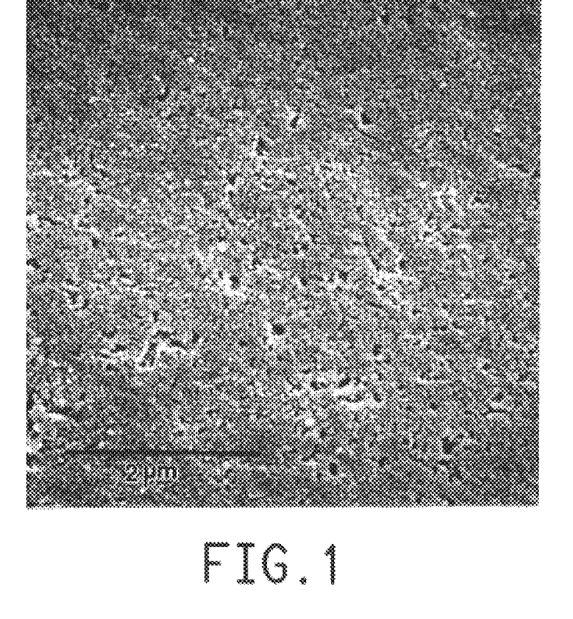
FIG. 1 is a scanning electron micrograph of a microcomposite prepared by the process of the present invention (see Example 1) using a liquid composition consisting essentially of water and a highly fluorinated ion-exchange polymer and a solution consisting essentially of water and a silicate. The microcomposite was calcined at 600° C. which removes the polymer and the new porosity observed indicates the original dispersion of the polymer within the microcomposite.

The polymer within a microcomposite can be removed (via calcination to 600° C.) in order to examine its dispersion by using Scanning Electron Microscopy (SEM) with energy dispersive X-ray analysis. The new porosity observed indicates the original dispersion fo the polymer within the composite. The SEMs can be obtained after heating the prepared microcomposite to about 600° C. for about 2 hours in air. The heated material (now with the polymer removed on heating) can be placed in epoxy and polished to give a flat surface. A suitable scanning electron microscope is Hitachi SEM S 800. A calcined microcomposite of the present invention reveals voids where the aggregates were dispersed within the microcomposite which aggregates are dispersed in a fairly uniform manner throughout the silica (see FIG. 1). In contrast, a microcomposite prepared from an alkoxide solution (see WO95/19222) reveals voids which correspond to finer domains of PFIEP highly dispersed throughout the silica. As indicated by mercury porosimetry, voids left by the calcination of the polymer of the present invention are in the range of about 0.2 to 0.5 microns in size; however, in the case of the alkoxide derived materials these holes are <0.1 microns.

Figure 3:
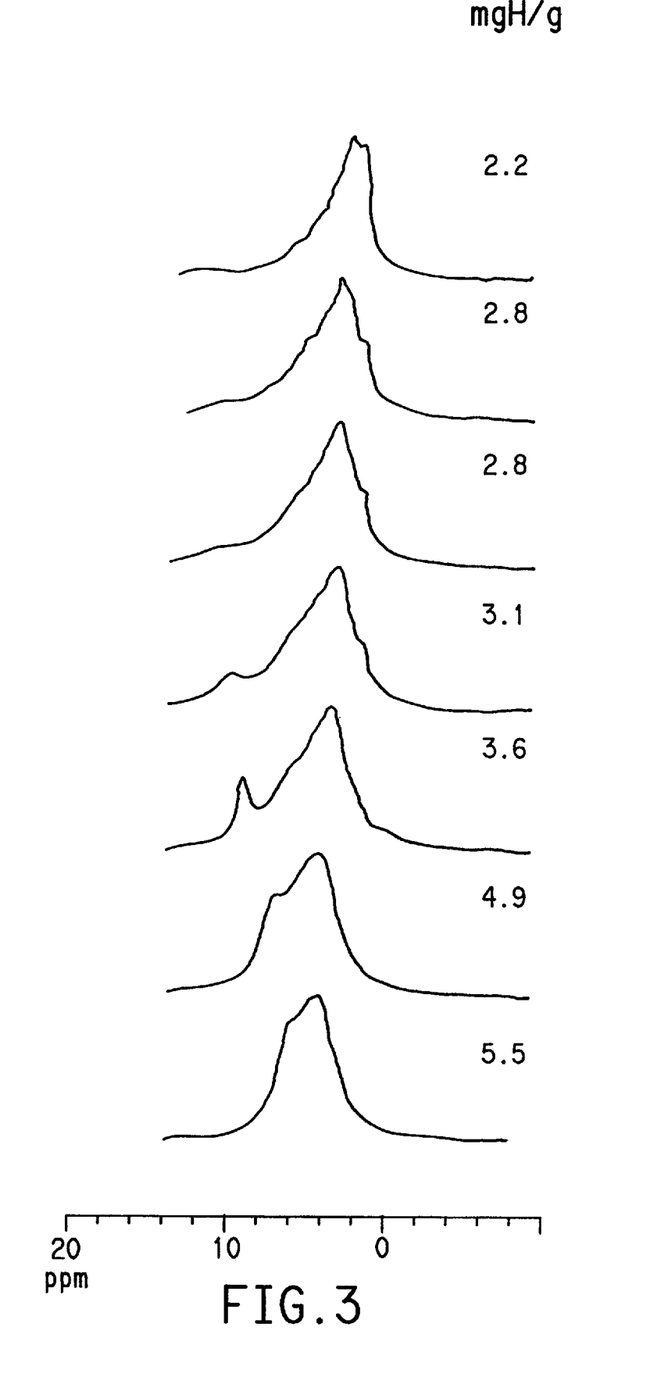
FIG. 3 is MAS proton NMR for a microcomposite of the present invention (see Example 1).
Figure 4:
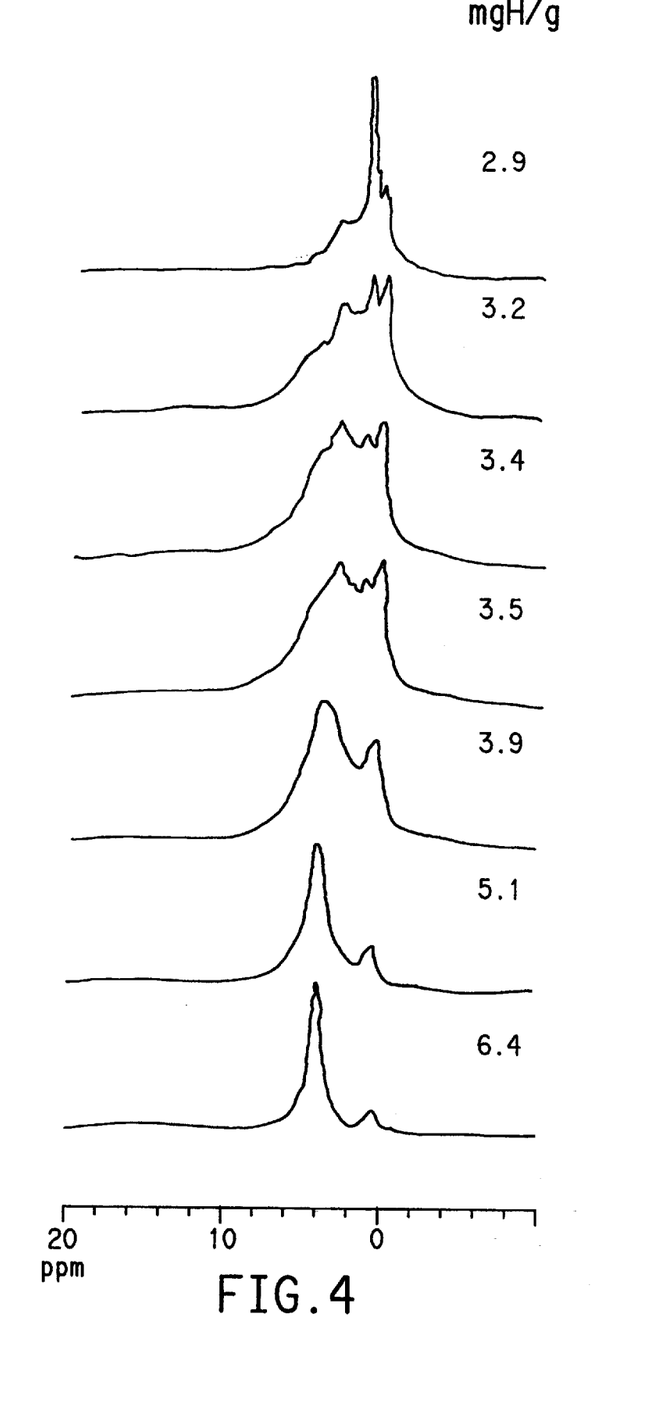
FIG. 4 is MAS proton NMR for a microcomposite prepared using an alkoxide solution (see Comparative Example B).

In FIGS. 3 and 4, the MAS proton NMR of the microcomposite of Example 1 and Comparative Example B (at various levels of water) are shown. FIG. 3 reveals that the silicate derived material of the present invention appears more Nafion®-like. The protons of the sulfonic acid within Nafion® appear at about 10–12 ppm and upon addition of water this moves to lower ca. 5 ppm. Interestingly, in the case of the alkoxide derived microcomposite (FIG. 4), a peak in the range 5–12 ppm (peaks at lower ppm are due to the silica) is not seen. However, in the proton NMR of the silicate derived materials of the present invention (FIG. 3), the proton NMR of the sulfonic acid falls in the expected range (the small size is due to the low concentration relative to the silica). Thus, as the polymer of the present invention becomes more aggregated, it becomes more Nafion® like. However, the aggregate size is still orders of magnitude smaller than the pure polymer and therefore general activity is increased. It is believed that this aggregation of the particles of polymer within the silica network of the present microcomposite is responsible for providing its higher activity in a number of catalytic reactions.

The present invention further provides an improved process for the alkylation of an aromatic hydrocarbon, such as benzene with propylene or benzene with a $C_{10}$–$C_{14}$ olefin, for example 1-dodecene, wherein the improvement comprises using a catalytic amount of the microcomposite of the present invention. In such a reaction, the desired alkyl substitutent precursor compound, aromatic compound and the microcomposite catalyst, which can be predried, are charged into a reactor. The reaction can be carried out at a temperature of about 70–80° C. under ambient pressure. The microcomposite of the present invention is significantly more active than a microcomposite of WO95/19222 (see Example 7).

The present invention further provides an improved process for the acylation of an aromatic hydrocarbon, such as m-xylene with benzoyl chloride, wherein the improvement comprises using a catalytic amount of the microcomposite of the present invention. In such a reaction, the desired substituent precursor compound, aromatic compound and the microcomposite catalyst, which can be predried, are charged into a reactor. The reaction can be carried out at a temperature of about 140° C. under ambient pressure.

The present invention further provides an improved process for the isomerization of an olefin, such as 1-dodecene, wherein the improvement comprises using a catalytic amount of the microcomposite of the present invention. In such a reaction, the olefin, the microcomposite catalyst, which can be predried, and an organic solvent such as decane, are charged into a reactor. The reaction can be carried out at a temperature of about 75° C. under ambient pressure.

The present invention also provides an improved process for the decomposition of cumene hydroperoxide wherein the improvement comprises using a catalytic amount of the microcomposite prepared by the process of the present invention. In the formation of cumene, the reaction rate when using a catalytic amount of a microcomposite of the present invention is very efficient under mild conditions (about 50° C.). For this particular reaction, the activity is very high with clean conversion.

The microcomposites prepared by the present process are also usefull as ion exchange resins, and as catalysts for alkylating aliphatic hydrocarbons; for sulfonating or nitrating organic compounds; and for oxyalkylating hydroxylic compounds. Other catalytic applications for the microcomposites of the present invention comprise hydrocarbon isomerization and polymerization; carbonylation and carboxylation reactions; hydrolysis and condensation reactions; esterifications and etherifications; hydrations and oxidations; oligomerizations; aromatic benzylation; and metathesis reactions.

EXAMPLES

NAFION® solutions and NAFION® resin can be purchased from Aldrich Chemical Co., Milwaukee, Wis., or fluorinated polymer ion-exchange solutions generally can be prepared using the procedure of U.S. Pat. Nos. 5,094,995 and U.S. Pat. No. 4,433,082. The NAFION® polymer solution referred to in the examples below is, unless otherwise noted, NAFION® NR005, a NAFION® solution available from DuPont Fluoroproducts, Fayetteville, N.C., and also known as NAFION® SE-5110. and is prepared from resin which is approximately 6.3 tetrafluoroethylene molecules for every perfluoro (3,6-dioxa-4-methyl-7-octene sulfonyl fluoride) molecule ($CF_2=CF-O-[CF_2CF(CF_3)]-O-CF_2CF_2-SO_2F$ and has an equivalent weight of approximately 1070.

Example 1

A solution of NAFION® polymer consisting essentially of the polymer and water only (polymer solution) was prepared by taking a 5 wt % NAFION® polymer water/alcohol containing solution and removing the alcohol by distillation. After the alcohol (propanol) was removed, the polymer solution became concentrated to 12 wt %. 25 g of the 12 wt % polymer solution was added to water to bring the total weight to 100 g. This gave a polymer concentration of about 3 wt %. A 10 wt % sodium silicate solution was prepared by adding 70 g of sodium silicate (with about 29 wt % silica) to water to bring the total weight to 200 g. The polymer solution was added to the stirred sodium silicate solution over 2 mins and then stirred for an additional 5 mins. To this combined solution, 52 g of 3.5M HCl was added giving a pH in the range of 7–7.5. The system gelled in about 5–10 seconds. The gel was placed in an oven and dried at a temperature of about 95–100° C. over a period of about 2 days. The hard glasslike product was ground and passed through a 10-mesh screen.

The solid was then treated as follows: The solid was washed with 2 liters of 25 wt % nitric acid, and the mixture was gently stirred for 12 hrs and the acid was decanted and then replaced with deionized water (2 liters) and stirred for a further 12 hrs. The solid was filtered and resuspended in 2 liters of 25 wt %/ nitric acid for a further 12 hrs followed by washing with water (2 liters, stirred for 12 hrs). The process of acid and water washing was repeated for a third time, and the material was filtered and then dried in a vacuum at 110° C. overnight.

The solid microcomposite (about 80 g) was found to contain about 12 wt % of the polymer as shown by thermogravimetric analysis (TGA). (The polymer loading was determined via TGA by heating the solid up to 800° C. and measuring the weight loss between 400–600° C.). (See also FIG. 1 for an SEM of the microcomposite after calcination and FIG. 3 for its proton MAS spectra.)

The reaction rate (mM/gCat/hr) for cumene formation via benzene propylation (see Example 7 for reaction process conditions) was 34.7.

Example 2

A NAFION® polymer solution consisting essentially of the polymer and water (polymer solution) was prepared by taking a 5 wt % NAFION® water/alcohol containing solution, and removing the alcohol by distillation. After the alcohol (propanol) was removed, the polymer solution became concentrated to 12 wt %. 25 g of the 12 wt % polymer solution was added to water to bring the total weight to 100 g. This gave a polymer concentration of about 3 wt %. A 10 wt % sodium silicate solution was prepared by adding 70 g of sodium silicate (with about 29 wt % silica) to water to bring the total weight to 200 g. The sodium silicate solution was stirred and both the polymer solution and 52 g of 3.5M HCl was added (using a separate beaker) to the sodium silicate solution at the same time giving a pH in the range of 7–7.5. The system gelled in about 5–10 secs. The gel was placed in an oven and dried at a temperature of about 95–100° C. over a period of about 2 days. The hard grasslike product was ground and passed through a 10-mesh screen. The solid was then treated as described in Example 1. The solid (about 80 g) was found to contain about 12 wt % of the polymer as shown by TGA. The reaction rate (mM/gCat/hr) for cumene formation via benzene propylation (see Example 7 for reaction conditions) was 22.9. The amount of benzene converted to cumene was 2.32%).

Example 3

A NAFION® polymer solution consisting essentially of the polymer and water (polymer solution) was prepared by taking a 5 wt % NAFION® polymer water/alcohol containing solution, and removing the alcohol by distillation. After the alcohol (propanol) was removed, the polymer solution became concentrated to 12 wt %. 25 g of the 12 wt % polymer solution was added to water to bring the total weight to 30 g. This gave a polymer concentration of about 10 wt %. A 10 wt % sodium silicate solution was prepared by adding 70 g of sodium silicate (with about 29 wt % silica) to water to bring the total weight to 200 g. The sodium silicate solution was stirred and added to the polymer solution and the combined solution was left to stir for 10 mins. 52 g of 3.5M HCl was added (using a separate beaker) to the combined solution giving a pH of 7.4. The system gelled in about 4 secs. The gel was placed in an oven and dried at a temperature of about 95–100° C. over a period of about 2 days. The hard glasslike product was ground and passed through a 10-mesh screen. The solid was then treated as described in Example 1. The solid microcomposite (about 80 g) was found to contain about 12 wt % of the polymer as shown by TGA. The reaction rate (mM/gCat/hr) for cumene formation via benzene propylation (see Example 7 for reaction process conditions) was 44. The amount of benzene converted to cumene was 4.44%.

Example 4

A NAFION® polymer solution consisting essentially of the polymer and water (polymer solution) was prepared by dissolving NAFION® resin in water at 230° C. for 3 hrs under pressure to give a 20 wt % containing solution. 16 g of the 20 wt % polymer solution and 84 g water was added to make 100 g of a 3.2 wt % polymer solution. A 10 wt % sodium silicate solution was prepared by adding 70 g of sodium silicate (with about 29 wt % silica) to water to bring the total weight to 200 g. The sodium silicate solution was stirred and added to the polymer solution, and the combined solution was left to stir for 10 mins. 52 g of 3.5M HCl was added to the combined solution giving a pH of 8.1. The system gelled in about 9 secs. The gel was placed in an oven and dried at a temperature of about 95–100° C. over a period of about 2 days. The hard glasslike product was ground and passed through a 10-mesh screen. The solid was then treated as described in Example 1. The solid microcomposite (about 80 g) was found to contain about 12 wt % of the polymer as shown by TGA. The reaction rate (mM/gCat/hr) for cumene formation via benzene propylation (see Example 7 for reaction process conditions) was 32. The amount of benzene converted to cumene was 3.46%.

Example 5

A NAFION® polymer solution consisting essentially of the polymer and water (polymer solution) was prepared by dissolving NAFION® resin in water at 230° C. under pressure to give a 20 wt % containing polymer solution. 16 g of the 20 wt % PFIEP solution and 15 g water was added to make 31 g of a 10 wt % polymer solution. A 10 wt % sodium silicate solution was prepared by adding 70 g of sodium silicate (with about 29 wt % silica) to water to bring the total weight to 200 g. The sodium silicate solution was stirred and added to the polymer solution, and the combined solution was left to stir for 10 mins. 52 g of 3.5M HCl was added to the combined solution giving a pH of 7.9. The system gelled in about 7 secs. The gel was placed in an oven and dried at a temperature of about 95–100° C. over a period of about 2 days. The hard glasslike product was ground and passed through a 10-mesh screen. The solid was then treated as described in Example 1. The solid (about 80 g) was found to contain about 12 wt % of the polymer as shown by TGA. The reaction rate (mM/gCat/hr) for cumene formation via benzene propylation (see Example 7 for reaction process conditions) was 45. The amount of benzene converted to cumene was 3.9%.

Example 6

A NAFION® polymer solution consisting essentially of the polymer an water (polymer solution ) was prepared by taking a 5 wt % NAFION® polymer water/alcohol containing solution and removing the alcohol by distillation. After the alcohol (propanol) was removed, the solution became concentrated to 12 wt %. 60 g of the 12 wt % polymer solution was added to water to bring the total weight to 100 g. This gave a polymer concentration of about 7.2 wt %. A 10 wt % sodium silicate solution was prepared by adding 70 g of sodium silicate (with about 29 wt % silica) to water to bring the total weight to 200 g. The polymer solution was added to the stirred sodium silicate solution in one batch, and then the combined solution was stirred for a further 5 mins. To this combined solution, 52 g of 3.5M HCl was added giving a pH in the range of 7.2. The system gelled in about 5–10 seconds. The gel was placed in an oven and dried at a temperature of about 95–100° C. over a period of about 2 days. The hard grasslike product was ground and passed through a 10-mesh screen. The solid was then treated as described in Example 1. The solid (about 80 g) was found to contain about 25 wt % of the polymer as shown by TGA. The reaction rate (mM/gCat/hr) for cumene formation via benzene propylation (see Example 7 for reaction process conditions) was 87. The amount of benzene converted to cumene was 9.84%.

Comparative Example A

A sodium silicate solution was treated with a Dowex ion exchange resin. 140 g of the sodium silicate solution was added to water (285 ml) to give a weight of 425 g. The sodium silicate solution was added slowly with cooling (ice) to 240 g of Dowex cation exchange resin to which 40 g of water had been added. The pH was kept near 3. (This is a titration reaction where the sodium silicate is a base and the $H^+$ form of the Dowex resin is an acid. As long as the resin is not saturated in the presence of salt the solution will be acidic. The pH can be varied by changing the rate of addition of the base, sodium silicate.) After all of the sodium silicate solution had been added, the resin was removed via filtration yielding a solution of polysilicic acid. 150 g of the polysilicic acid solution was added to 60 g of a 3 wt % NAFION® polymer water only solution prepared by dissolving NAFION® polymer in water at 255° C. for 3 hrs under pressure. The pH of the combined solution was adjusted to 7 by adding 2M NaOH. The system gelled in about 1–2 mins. The gel was placed in an oven and dried at a temperature of about 95–100° C. over a period of about 2 days. The hard grasslike and clear product was ground and passed through a 10-mesh screen. The solid was then treated as described in Example 1. The solid (about 15 g) was found to contain about 13 wt % of the polymer as shown by TGA. The reaction rate (mM/gCat/hr) for cumene formation via benzene propylation (see Example 7 for reaction process conditions) was 2.05. The amount of reactant converted to cumene was 0.28%.

The example shows how the activity of the microcomposite changes based on the preparation route. Using sodium silicate and water only polymer solutions (Examples 1–6) give high alkylation activity compared to the process of this example which uses polysilicic acid and water only polymer solution and results in low alkylation activity.

Figure 2:
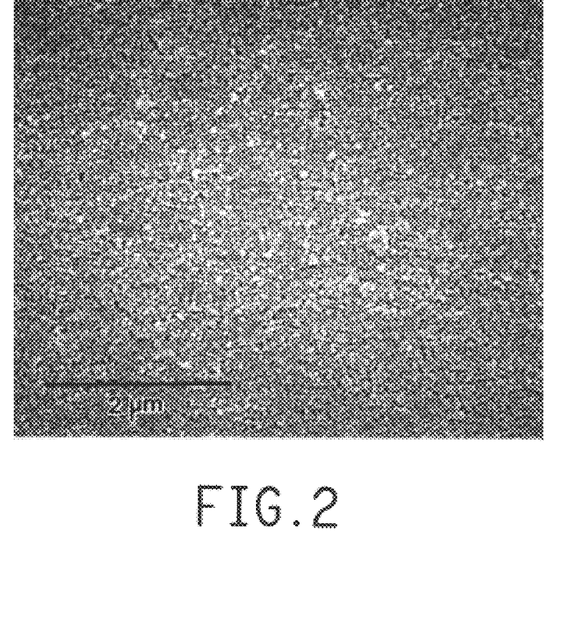
FIG. 2 is a scanning electron micrograph of a microcomposite prepared using a liquid composition comprising PFIEP, water and alcohol and an alkoxide solution (see Comparative Example B). The microcomposite was calcined at 600° C. to indicate the dispersion of the PFIEP.

Comparative Example B 240 g of tetraethylorthosilicate $(Si(OEt)_4)$, 69 g of distilled water and 1.15 g of 3.5M HCl was stirred for 2 hours to give a clear solution (TEOS solution). To 240 ml of a NAFION® polymer water/alcohol solution (which contained 5% NAFION® polymer by weight) was added 120 ml of 0.4M NaOH while the NAFION® polymer solution was stirred. The TEOS solution was then added rapidly to the stirred NAFION® polymer containing solution. After a few seconds, the whole system gelled. The gel was placed in an oven and dried at a temperature of about 95–100° C. over a period of about 2 days. The hard glasslike product was ground and passed through a 10-mesh screen. The solid was then treated as described in Example 1. The solid (about 80 g) was found to contain about 15 wt % of the NAFION® polymer as shown by TGA. (See also FIG. 2 for an SEM of the microcomposite after calcination and FIG. 4 for its proton MAS spectra.)

The reaction rate (mM/gCat/hr) for cumene formation via benzene propylation (see Example 7 for reaction process conditions) was 5.5.

Comparative Example C 240 g of tetraethylorthosilicate (Si(OEt)$_4$), 69 g of distilled water and 1.15 g of 3.5M HCl was stirred for 2 hours to give a clear solution (TEOS solution). To 240 ml of a NAFION® polymer water/alcohol solution (which contained 5% NAFION® polymer by weight) was added 120 ml of 0.4M NaOH over about 10 mins while the NAFION® polymer solution was stirred. The TEOS solution was then added rapidly to the stirred NAFION® polymer containing solution. After a few seconds, the whole system gelled. The gel was placed in an oven and dried at a temperature of about 95–100° C. over a period of about 2 days. The hard glasslike product was ground and passed through a 10-mesh screen. The solid was then treated as described in Example 1. The solid (about 80 g) was found to contain about 15 wt % of the NAFION® polymer as shown by TGA. The reaction rate (mM/gCat/hr) for cumene formation via benzene propylation (see Example 7 for reaction process conditions) was 2.87. The amount of benzene converted to cumene was 0.34%.

Comparative Example D 240 g of tetraethylorthosilicate (Si(OEt)$_4$), 33 g of distilled water and 3 g of 0.04M HCl was stirred for 1 hr to give a clear solution (TEOS solution). To 300 ml of a NAFION® polymer water/alcohol solution (which contained 5% NAFION® polymer by weight) was added 150 ml of 0.4M NaOH over about 15 mins while the NAFION® polymer solution was stirred. The TEOS solution was then added rapidly to the stirred NAFION® polymer containing solution. After a few seconds, the whole system gelled. The gel was placed in an oven and dried at a temperature of about 95–100° C. over a period of about 2 days. The hard grasslike product was ground and passed through a 10-mesh screen. The solid was then treated as described in Example 1. The solid (about 80 g) was found to contain about 15 wt % of the NAFION® polymer as shown by TGA. The reaction rate (mM/gCat/hr) for cumene formation via benzene propylation (see Example 7 for reaction process conditions) was 1.28. The amount of benzene converted to cumene was 0.16%.

Comparative Example E

Distilled water was added to 136 g of sodium silicate (which contained about 29 wt % in silica) to give a final weight of 425 g and a final silica concentration of about 9 wt %. This solution was added dropwise to 240 g of a Dowex cation exchange resin in the acid form to which 40 g of water had been added. The resin was cooled in ice/acetone during the addition. The sodium silicate was added over about 1 hr while monitoring the pH change and keeping the pH in the range of about 2.5 to 4. After the final addition, the mixture was stirred for 5 mins and then filtered through a 50-mesh screen. 150 g of the filtered solution was used in the preparation of the gel. The above ion exchange converts the sodium silicate to a solution of polysilicic acid (with most of the sodium ions removed). 150 g of the polysilicic acid solution was added rapidly to 60 g of a 3 wt % NAFION® polymer solution which had been prepared in water only (polymer solution). The polymer solution was prepared by heating NAFION® polymer resin in water at 270° C. for a period of about 3 hrs to give a concentration of polymer of about 20 wt % which was diluted down to 3 wt %. To the combined polymer and polysilicic acid solutions, 2.0M NaOH was added (few mls) to adjust the pH to 7, and the solution was left to stir. The solution gelled after a few mins. The gel was placed in an oven and dried at a temperature of about 95–100° C. over a period of about 2 days. The hard glasslike product was ground and passed through a 20-mesh screen. The solid was then treated as described in Example 1. The solid (about 80 g) was found to contain about 13 wt % of the polymer as shown by TGA. The reaction rate (mM/gCat/hr) for cumene formation via benzene propylation (see Example 7 for reaction process conditions) was 1.46. The amount of benzene converted to cumene was 0.19%.

Comparative Example F

Distilled water was added to 136 g of sodium silicate (which contained about 29 wt % in silica) to give a final weight of 425 g and a final silica concentration of about 9 wt %. This solution was added dropwise to 240 g of a Dowex cation exchange resin in the acid form to which 40 g of water had been added. The resin was cooled in ice/acetone during the addition. The sodium silicate was added over about 1 hr while monitoring the pH change and keeping the pH in the range of about 2.5 to 4. After the final addition, the mixture was stirred for 5 mins and then filtered through a 50-mesh screen. 150 g of the filtered solution was used in the preparation of the gel. 150 g of the polysilicic acid solution was added rapidly to 60 g of a 3 wt % NAFION® polymer water only solution (polymer solution). The polymer solution was prepared by taking the NAFION® solution as described in Comparative Example A and adding water to dilute the solution down to 3 wt %. The solution was then distilled at 100–110° C. to remove the alcohols periodically replacing the lost volume with water to maintain the polymer concentration to about 3 wt %. At these distillation temperatures substantially all of the alcohol (propanol) is removed giving a 3 wt % polymer solution which is water based. To the combined polymer and polysilicic acid solutions, 2.0M NaOH was added (few mls) to adjust the pH to 7, and the solution was left to stir. The solution gelled after a few mins. The gel was placed in an oven and dried at a temperature of about 95–100° C. over a period of about 2 days. The hard grasslike product was ground and passed through a 10-mesh screen. The solid was then treated as described in Example 1. The solid (about 80 g) was found to contain about 13 wt % of the polymer as shown by TGA. The reaction rate (mM/gCat/hr) for cumene formation via benzene propylation (see Example 7 for reaction process conditions) was 2.05. The amount of reactant converted to cumene was 0.128%.

Example 7

Catalytic Reaction Comparisons of Microcomposite Catalysts Prepared By Silicate/Water Only Route (Present Invention) VS. Alkoxide Route (WO95/19222)

The microcomposite of the present invention as prepared in Example 1 and the microcomposite prepared in Comparative Example B were used as catalysts in the following reactions.

1-Dodecene Isomerization to 2-, 3-, 4-, 5- and 6-Dodecenes: 10 g of 1-dodecene which was freshly distilled, 30 g of decane and 1 g of microcomposite catalyst which was predried were charged into a two-neck flask with a magnetic stir bar for mixing. Decane serves as solvent and internal standard for the GC analysis. Liquid samples were taken at certain time intervals and analyzed by GC. Very good material balances (>98%) were obtained and formation of oligomers were negligible under these conditions. The 1-dodecene reaction rates were calculated from the data obtained at low 1-dodecene conversions (<30%). The first order rates over the catalysts are listed in Table 1 below.

Benzene Propylation to Form Cumene: 50 g of benzene was charged into a three neck flask and bubbled with propylene gas (flow rate=200 cc/min). At the desirable reaction temperature (70° C.), the microcomposite catalyst was added to the reactor. The reaction rates are listed in Table 1. The silicate/water only route microcomposite was more than an order of magnitude more active than the alkoxide derived microcomposite catalyst. For this particular application, the microcomposite catalyzed reaction is much cleaner than the corrosive HF or $AlCl_3$ that are currently in use.

Linear Alkylbenzene (LAB) Formation: 10.0 g of 1-dodecene, 21.5 g benzene and 1 g of microcomposite catalyst were charged into a reactor. The reaction was carried out at 80° C. under ambient pressure. The reaction rates are listed in Table 1. The silicate/water-only microcomposite was significantly more active than the alkoxide derived microcomposite.

Friedel-Crafts Acylation: The acylation of m-xylene with benzoyl chloride to form benzophenones was carried out at 140° C. The reaction mixture contained 21.2 g m-xylene, 14.0 g benzoyl chloride and 1 g of catalyst. The reaction rates are listed in Table 1.

TABLE 1

Reaction Rates (mM/g.cat.hr)for Catalyzed Reactions in Liquid Phase

| Reaction | Microcomposite of Example 1 | Microcomposite of Comparative Example B |
|---|---|---|
| 1-Dodecene Isomerization | 190.0 | 153.0 |
| Benzene Propylation | 34.7 | 5.5 |
| LAB Formation | 41.4 | 5.8 |
| Friedel-Crafts Acylation | 108.0 | 24.0 |

What is claimed is:

1. A process for the preparation of a porous microcomposite which comprises a highly fluorinated ion-exchange polymer containing pendant sulfonate functional groups, said polymer existing as aggregated particles entrapped within and dispersed throughout a network of silica, wherein the weight percentage of the highly fluorinated ion-exchange polymer in the microcomposite is from about 0.1 to about 90 percent; said process comprising the steps of:

(a) preparing a liquid composition consisting essentially of water and a highly fluorinated ion-exchange polymer containing pendant sulfonate functional groups;

(b) contacting said liquid composition with a solution consisting essentially of water and a silicate selected from the group consisting of: sodium silicate, ammonium silicate, potassium silicate, and any combination thereof;

(c) allowing the silicate to form a network of silica; and (d) recovering the porous microcomposite.

2. The process of claim 1 wherein the silicate is sodium silicate.

3. The process of claim 1 wherein the highly fluorinated ion-exchange polymer is perfluorinated ion-exchange polymer prepared from a resin having an equivalent weight of about 800 to 2000, said resin comprising tetrafluoroethylene and perfluoro(3,6-dioxa-4-methyl-7-octenesulfonyl fluoride).

4. The process of claim 3 wherein the weight percent of perfluorinated ion-exchange polymer is about 10–15%.

5. The process of claim 1 wherein the size of the pores is about 0.5 mm to about 30 nm.

6. A porous microcomposite comprising a highly fluorinated ion-exchange polymer containing pendant sulfonate functional groups, said polymer existing as aggregated particles entrapped within and dispersed throughout a network of silica, wherein the weight percentage of the highly fluorinated ion-exchange polymer in the microcomposite is from about 0.1 to about 90 percent, said microcomposite prepared by the process of claim 1.

7. An improved method for the isomerization of an olefin the improvement comprising using a catalytic amount of a microcomposite of claim 6.

8. An improved method for the alkylation of an aromatic compound the improvement comprising using a catalytic amount of a microcomposite of claim 6.

9. An improved method for the acylation of an aromatic compound, the improvement comprising using a catalytic amount of a microcomposite of claim 6.

10. An improved method for decomposing cumene hydroperoxide, the improvement comprising using a catalytic amount of a microcomposite of claim 6.

* * * * *